US008003128B2

(12) United States Patent
Kreuter et al.

(10) Patent No.: US 8,003,128 B2
(45) Date of Patent: Aug. 23, 2011

(54) POLYLACTIDE NANOPARTICLES

(75) Inventors: Jörg Kreuter, Bad Homburg (DE);
Svetlana Gelperina, Moscow (RU);
Olga Maksimenko, Moscow (RU);
Alexander Khalanskiy, Moscow (RU)

(73) Assignee: LTS Lohmann Therapie-Systeme AG, Andernach (DE)

( * ) Notice: Subject to any disclaimer, the term of this patent is extended or adjusted under 35 U.S.C. 154(b) by 294 days.

(21) Appl. No.: 12/225,555

(22) PCT Filed: Mar. 13, 2007

(86) PCT No.: PCT/EP2007/002198
§ 371 (c)(1),
(2), (4) Date: Sep. 24, 2008

(87) PCT Pub. No.: WO2007/110152
PCT Pub. Date: Oct. 4, 2007

(65) Prior Publication Data
US 2009/0263491 A1 Oct. 22, 2009

(30) Foreign Application Priority Data
Mar. 24, 2006 (DE) .......................... 10 2006 013 531

(51) Int. Cl.
*A61K 9/16* (2006.01)
(52) U.S. Cl. ...................................................... 424/497
(58) Field of Classification Search ........................ None
See application file for complete search history.

(56) References Cited

U.S. PATENT DOCUMENTS

| 6,117,454 A | 9/2000 | Kreuter et al. | |
|---|---|---|---|
| 6,309,663 B1 | 10/2001 | Patel et al. | |
| 2005/0084456 A1* | 4/2005 | Tang et al. | 424/46 |
| 2005/0112188 A1* | 5/2005 | Eliaz et al. | 424/450 |
| 2006/0024248 A1* | 2/2006 | Spengler et al. | 424/49 |
| 2006/0141025 A1* | 6/2006 | Huang et al. | 424/451 |

FOREIGN PATENT DOCUMENTS

| EP | 1795185 | 6/2007 |
|---|---|---|
| WO | WO 9856361 | 12/1998 |
| WO | WO 2004/084871 | 10/2004 |
| WO | WO 2004/112695 | 12/2004 |

OTHER PUBLICATIONS

Mu et al "A novel controlled release formulation of the anticancer drug paclitaxel (Taxol): PLGA nanoparticles containing vitamin E TPGS" Journal of Controlled Release 86 (2003) p. 33-48.*

Dintaman, Jay M., et al.; "Inhibition of P-glycoprotein by d-alpha-tocopheryl polyethylene glycol 1000 succinate (TPGS);" *Pharmaceutical Research*, vol. 16, No. 10; Oct. 1999 (pp. 1550-1556).

Feng, S-S, et al; "Chemotherapeutic engineering: Application and further development of chemical engineering principles for chemotherapy of cancer and other diseases;" *Chemical Engineering Science*; vol. 58, No. 18; Sep. 2003 (pp. 4087-4114).

Muller, R.H., et al.; "Surface modification of i.v. injectable biodegradable nanoparticles with poloxamer polymers and poloxamine 908;" *International Journal of Pharmaceutics*; vol. 89, No. 1; 1993 (pp. 25-31).

Mu, et al.; "Application of TPGS in polymeric nanoparticulate drug delivery system;" *Colloids and Surfaces.*; vol. 47, No. 1; Jan. 15, 2006 (pp. 90-97).

Mu, et al.; "Vitamin E TPGS used as emulsifier in the solvent evaporation / extraction technique for fabrication of polymeric nanospheres for controlled release of paclitaxel;" *Journal of Controlled Release.*; vol. 80, No. 1-3; Apr. 23, 2002 (pp. 129-144).

Redhead, H.M., et al.; "Drug Delivery in poly(lactide-co-glycolide) nanoparticles surface modified with poloxamer 407 and poloxamine 908: In vitro characterisation and in vivo evaluation;" *Journal of Controlled Release*; vol. 70, No. 3; Feb. 23, 2001; (pp. 353-363).

Ruan, G, et al.; "Effects of material hydrophobicity on physical properties of polymeric microspheres formed by double emulsion process;" *Journal of Controlled Release*; vol. 84, No. 3; Dec. 5, 2002 (pp. 151-160).

Yoon, Jeong Park, et al.; "Surface-modified poly (lactide-co-glycolide) nanospheres for targeted bone imaging with enhanced labelling and delivery of radioisotope;" *Journal of Biomedical Materials Research*; vol. 67A, No. 3; 2003 (pp. 751-760).

Zhang, et al.; "Nanoparticles of poly(lactide)/vitamin E TPGS copolymer for Cancer Chemotherapy: Synthesis, formulation, characterization and in vitro drug release;" *Biomaterials*; vol. 27, No. 2; Jan. 2006 (pp. 262-270).

Mueller, R.H., et al.; "Surface modification of i.v. injectable biodegradable nanoparticles with poloxamer polymers and poloxamine 908;" *International Journal of Pharmaceutics*; vol. 89, No. 1; 1993 (pp. 25-31).

* cited by examiner

*Primary Examiner* — Robert A Wax
*Assistant Examiner* — Bethany Barham
(74) *Attorney, Agent, or Firm* — D. Peter Hochberg; Sean F. Mellino; Daniel J. Smola

(57) ABSTRACT

A drug targeting system for administering a pharmacologically active substance to the central nervous system of a mammal across the animal's blood brain barrier. The drug targeting system comprises nanoparticles made of poly(DL-lactide) and/or poly(DL-lactide-co-glycolide), a pharmacologically active substance which is absorbed to, adsorbed to, and/or incorporated into the nanoparticles, and either contains TPGS or comprises a pluronic 188 surfactant coating deposited on the drug-loaded nanoparticles.

7 Claims, 2 Drawing Sheets

POLYLACTIDE NANOPARTICLES

CROSS-REFERENCE TO RELATED APPLICATIONS

This application is a National Stage application of International Application No. PCT/EP2007/002198, filed on Mar. 13, 2007, which claims priority of German application number 10 2006 013 531.8, filed on Mar. 24, 2006, both of which are incorporated herein by reference in their entireties.

BACKGROUND OF THE INVENTION

1. Field of the Invention

The present invention relates to systems for targeting pharmacologically active substances to the central nervous system of a mammal. Particularly, the present invention concerns nanoparticulate drug targeting systems which are capable of crossing the blood-brain barrier of a mammal. More particularly, the present invention pertains to drug-loaded nanoparticles on the basis of polylactides and/or polylactide-coglycolides, to methods for producing drug-loaded nanoparticles on the basis of polylactides and/or polylactide-coglycolides, and to the use of drug-loaded nanoparticles on the basis of polylactides and/or polylactide-coglycolides for the treatment of diseases or disorders of the central nervous system, in particular to the treatment of neuronal cancer.

2. Description of the Prior Art

Diseases and disorders of the central nervous system (CNS) may be treated by administering drugs that have an impact on nervous system function. These drugs are usually given to a patient in need thereof by conventional oral administration or by injection. Unfortunately, many drugs such as adenosine, β-endorphine, synthetic analogs of endogenous peptides, excitatory and inhibitory amino acids and trophic factors do not pass the blood-brain barrier at all or only in amounts insufficient to be therapeutically efficient. Such drugs are only therapeutically effective when administered directly into the brain, for instance by direct CNS infusion.

As an alternative to direct CNS infusion, U.S. Pat. No. 6,117,454 suggests a method for transmitting pharmaceutically active substances across the blood-brain barrier of a mammal, wherein nanoparticles shall be used to target drugs or diagnostic agents to the CNS by crossing the blood-brain barrier. Pursuant to U.S. Pat. No. 6,117,454, a drug is added during or after polymerization of suitable monomers such as butyl cyanoacrylate to be either incorporated into or adsorbed onto the surface of the resulting poly-butyl cyanoacrylate nanoparticles. These nanoparticle-drug complexes are said to be able to cross the blood-brain barrier and to target the drug to the CNS if they are coated with an appropriate surfactant. Polyoxyethylene 20 sorbitan monolaurate (TWEEN® 20), polyoxyethylene 20 sorbitan monopalmitate (TWEEN® 40), polyoxyethylene 20 sorbitan monostearate (TWEEN® 60), polyoxyethylene 20 sorbitan monooleate (TWEEN® 80), and mixtures thereof are claimed to be appropriate surfactants that enable the drug-loaded poly-butyl cyanoacrylate nanoparticles to cross the blood-brain barrier.

It is proposed in this document that basically any drug could be incorporated into or bound to the surfactant-coated nanoparticles and be delivered to the brain without the need to alter the structure of the drug. Hence, it appears that U.S. Pat. No. 6,117,454 provides the first universal method of targeting a drug to the CNS by crossing the blood-brain barrier.

Concerns about the probability of toxic side effects of the surfactants used to coat the resulting poly-butyl cyanoacrylate nanoparticles and the desire to simplify the production process of drug-loaded nanoparticles led to the development of a simplified and potentially less toxic method of nanoparticle fabrication as disclosed in WO 98/56361.

WO 98/56361 teaches that surfactants are no longer required if nanoparticles are prepared by using Dextran 12.000 or polysorbate 85 (polyoxyethylene 20 sorbitan trioleate; TWEEN® 85) as stabilizers during the polymerization of butylcyanoacrylate monomers. It was shown that dalargin being adsorbed onto the stabilized polybutylcyanoacrylate nanoparticles can pass the blood-brain barrier, and that amitriptyline being adsorbed to polysorbate 85-stabilized nanoparticles accumulates to higher concentrations in the brain than amitriptyline as such.

However, there is still a demand for alternative systems of drug-loaded nanoparticles for targeting drugs to the CNS of a mammal across the blood-brain barrier, in order to improve one or more of efficacy, specificity, toxicity, and simplicity of preparation.

SUMMARY OF THE PRESENT INVENTION

It was therefore an object of the present invention to provide an improved drug targeting system for administering a pharmacologically active substance to the central nervous system of a mammal across this mammal's blood-brain barrier.

This object was achieved by a drug targeting system comprising nanoparticles based on poly(DL-lactide) (PLA) and/or poly(DL-lactide-co-glycolide) (PLGA), wherein a pharmacologically active substance is absorbed to, adsorbed to, and/or incorporated into the nanoparticles, and wherein the nanoparticles either contain TPGS or comprise a poloxamer 188 surfactant coating that is deposited on the drug-loaded nanoparticles.

It should be understood that the term "drug-loaded nanoparticles" as used herein refers to nanoparticles comprising a pharmacologically active substance. A pharmacologically active substance can either be a therapeutic agent or a diagnostic agent. Hence the "drug-loaded nanoparticles" of the invention comprise at least one therapeutic agent and/or at least one diagnostic agent being absorbed to, adsorbed to, or incorporated into said nanoparticles.

The term "blood-brain barrier" as used herein refers to the blood-brain barrier as such, i.e. the endothelium of the brain vessels, the basal membrane and neuroglial cells. The blood-brain barrier serves to control the transfer of substances into the brain. The term "blood-brain barrier" as used herein refers to the blood-spinal barrier and also to the blood-retina barrier.

Polylactides (PLA), also called polylactic acids, are polyesters on the basis of lactic acid. Polylactides are polyhydroxyacids. They are biocompatible and biodegradable.

The properties of polylactides depend primarily on their molecular weight, degree of crystallinity, and the portion of copolymers, if applicable. The glass transition temperature, the melting temperature, the tensile strength and the E-module of the polylactides increase, but the breaking elongation decreases as the molecular weight of the polylactides increases.

Polylactides can be obtained by ring-opening polymerization of lactide. The ring-opening polymerisation is performed at temperatures between 140 and 180° C. in the presence of stannous octoate catalyst. Polylactides with high molecular weight can be easily produced by this method.

In addition, high molecular weight and pure polylactides can be generated directly from lactic acid by the so-called polycondensation.

Polylactide coglycolides (PLGA) are biodegradable polymers that consist of lactic acid linked with glycolic acid, the respective percentages of which play a major role in the rate of drug release. The ratio of lactide to glycolide may be from 90:10 to 10:90, with ratios of from 20:80 to 80:20 being preferred and ratios of from 40:60 to 60:40 being more preferred, and a ratio of 50:50 being most preferred. Lactide is optically active, and any proportions of D and L isomers may be present, ranging from pure D-lactide to pure L-lactide, with racemates comprising 50% D-lactide and 50% L-lactide.

Poloxamers are nonionic polyoxyethylene-polyoxypropylene block co-polymers with the general formula $HO(C_2H_4O)_a(—C_3H_6O)_b(C_2H_4O)_aH$. They are available in different grades which vary from liquids to solids. Poloxamers are used as emulsifying agents, solubilizing agents, surfactants, and as wetting agents for antibiotics.

Poloxamer 188 (PLURONIC® F68 (BASF Corp.)) is a difunctional block copolymer surfactant terminating in primary hydroxyl groups. It is a non-ionic surfactant being relatively non-toxic. Poloxamer 188 has an average molecular weight of 8,400, a viscosity of 1,000 cps at 77° C., a cloud point (10% aqueous) of >100° C., and a HLB value of >24.

Poloxamer 185 (PLURONIC® P65 (BASF Corp.)) is a difunctional block copolymer surfactant terminating in primary hydroxyl groups. It is a non-ionic surfactant being relatively non-toxic. PLURONIC® P65 has an average molecular weight of 3,400, a viscosity of 180 cps at 60° C., a cloud point (10% aqueous) of 80-84° C., and a HLB value of 12-18.

PLURONIC® P85 (BASF Corp.), also designated as poloxamer 235, is a difunctional block copolymer surfactant terminating in primary hydroxyl groups. It is a non-ionic surfactant being relatively non-toxic. PLURONIC® P85 has an average molecular weight of 4,600, a viscosity of 310 cps at 60° C., a cloud point (10% aqueous) of 83-89° C., and a HLB value of 12-18.

Polysorbate 80 (polyoxyethylene-sorbitan-monooleate, TWEEN® 80) is a non-ionic surfactant. Polysorbate 80 has an average molecular weight of 1,300, a viscosity of 375-480 mPa·s at 25° C., and a HLB value of 14-16.

TPGS (D-α-tocopheryl polyethylene glycol 1000 succinate is a water-soluble derivative of d-α-tocopheryl succinate. TPGS is used as a water-soluble delivery form of vitamin E for persons with fat malabsorption syndromes, such as chronic childhood cholestasis. It is also used as an absorption and bioavailability enhancer for the water-insoluble HIV protease inhibitor amprenavir and fat-soluble vitamins such as vitamin D. TPGS is synthesized by esterifying d-α tocopheryl succinate with polyethylene glycol (PEG) 1000 (the molecular weight of PEG 1000 is approximately 1,000 daltons). Its molecular weight is approximately 1,513 daltons. It is a pale yellow, waxy solid substance that is amphipathic and hydrophilic. The pharmacokinetics of TPGS is still being worked out. TPGS is more efficiently absorbed from the lumen of the small intestine following ingestion than other forms of vitamin E. The mechanism of its absorption into enterocytes remains unclear. TPGS, because of its amphipathic nature (has both hydrophilic and lipophilic ends), forms its own micelles and thus does not require bile salts to do so. TPGS may enhance the absorption of lipophilic drugs if formulated together with these drugs. Further, the enhancement of the oral bioavailability of some drugs when co-administered with TPGS may, in part, be due to inhibition of P-glycoprotein in the intestine.

The drug-loaded PLA nanoparticles and PLGA nanoparticles of the invention can be used to target the drug across the blood-brain barrier to the central nervous system, and for treating diseases or disorders of the central nervous system or for the manufacturing of a medicament for treating diseases or disorders of the central nervous system.

DETAILED DESCRIPTION OF THE PRESENT INVENTION

Figure 1:
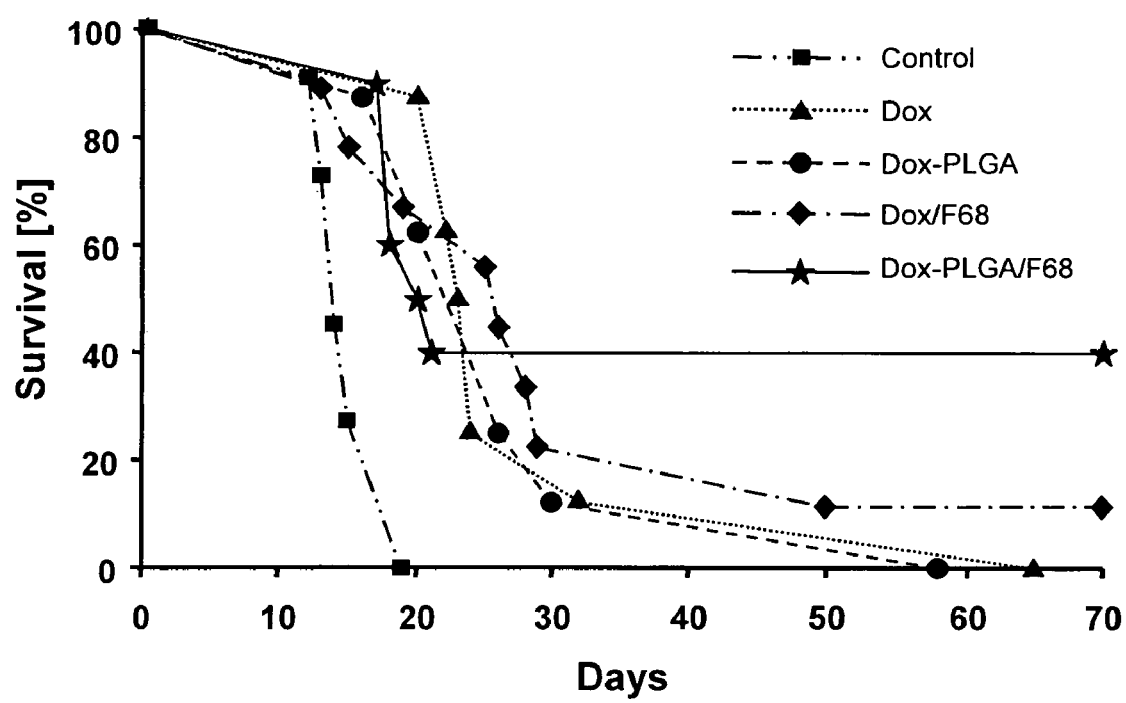
FIG. 1 shows a graph which illustrates the survival of rats bearing intracranial 101/8 glioblastoma after chemotherapy with various nanoparticle preparations comprising doxorubicin.

The drug-loaded PLA nanoparticles and PLGA nanoparticles of the invention can be produced either by a) a high pressure homogenization-solvent evaporation technique or b) a double emulsion technique (water-in-oil-in-water emulsion).

a) High Pressure Homogenization-solvent Evaporation Technique

Typically, the polymer and the drug are dissolved in an organic solvent. This organic phase is slowly poured under stirring into an aqueous solution of a stabilizing agent. The mixture is then emulsified using a high speed shear homogenizer. The obtained primary emulsion is then passed through a high-pressure homogenizer at high pressure. The organic solvent is removed by either slow evaporation at ambient temperature and normal pressure under stirring, or by quick evaporation at reduced pressure. During the process, the nanodroplets solidify in the aqueous system.

The resulting nanosuspension is filtered through a glass-sintered filter. For storage a cryoprotecting agent is added, preferably 5% w/v of mannitol. The suspension is then filled in vials, frozen at −35° C., and subsequently freeze-dried.

If additional compounds, such as cetyl phosphate, potassium cholesteryl sulfate or tocopheryl succinate are to be used as emulsifiers and/or counter-ions in the preparation of the drug targeting system, the polymer and the lipid compound are solubilized in an organic solvent and the drug is dissolved in water. The organic and aqueous solutions are mixed and incubated at ambient temperature. The mixture is then poured into a stirred aqueous solution containing a stabilizing agent, and then further processed, as described above.

b) Double Emulsion Technique

Typically, the polymer is dissolved in an organic solvent and the drug is dissolved in water. The aqueous solution is added to the organic phase. The mixture is emulsified. The obtained w/o emulsion is added to an aqueous solution of a stabilizing agent and then further emulsified. The resulting coarse emulsion is passed through a high-pressure homogenizer. The homogenization step is repeated several times to produce a stable w/o/w emulsion. Then the organic solvent is removed by slow evaporation at ambient temperature and normal pressure.

It is possible to dissolve the drug and an additional emulsifier, such as γ-cyclodextrin, in water before adding the solution to the organic phase.

The obtained nanosuspension is filtered through a glass-sintered filter. For storage, a cryoprotecting agent is added, and the nanosuspension is filled in vials, frozen, and then freeze-dried.

The obtained nanoparticle formulations are to be tested for resuspendability, particle size, drug loading (theoretical), and drug content.

It should be understood that the detailed description and specific examples, while indicating preferred embodiments of the invention, are given by way of illustration only, since various changes and modifications within the spirit and the scope of the invention will become apparent to those skilled in the art from this description and the accompanying figure as well as from the claims.

The drug targeting system of the invention comprises nanoparticles on the basis of poly(DL-lactide) and/or poly(DL-lactide-co-glycolide), at least one pharmacologically active substance, and either contain TPGS or comprise a surfactant coating deposited on the drug-loaded nanoparticles, wherein the surfactant is poloxamer 188.

In a preferred embodiment, the nanoparticles of the drug targeting system have a diameter of below 1,000 nm, preferably a diameter of between 100 and 800 nm, most preferably a diameter of between 130 and 160 nm.

The PLA- and/or PLGA-based nanoparticles of the present invention can be loaded with virtually any pharmacologically active substance in order to administer the pharmacologically active substance, i.e. a therapeutic agent or a diagnostic agent, to the CNS of a mammal across the mammal's blood-brain barrier.

The therapeutic agent may be selected from the group consisting of drugs acting at synaptic and neuroeffector junctional sites; general and local analgesics and anesthetics; hypnotics and sedatives; drugs for the treatment of psychiatric disorders such as depression and schizophrenia; anti-epileptics and anticonvulsants; drugs for treating Huntington's disease, aging and Alzheimer's disease; excitatory amino acid antagonists and neurotropic factors and neuroregenerative agents; trophic factors; drugs aimed at the treatment of CNS trauma or stroke; drugs for the treatment of addiction and drug abuse; autacoids and anti-inflammatory drugs; chemotherapeutic agents for parasitic infections and microbial diseases; immunosuppressive agents and anti-cancer drugs; hormones and hormone antagonists; heavy metals and heavy metal antagonists; antagonists for nonmetallic toxic agents; cytostatic agents for the treatment of cancer; diagnostic substances for use in nuclear medicine; immunoactive and immunoreactive agents; transmitters and their respective receptor agonists and receptor antagonists, their respective precursors or metabolites; antibiotics, antispasmodics, antihistamines, antinauseants, relaxants, stimulants, "sense" and "anti-sense" oligonucleotides, cerebral dilators, psychotropics, anti-manics, vascular dilators and constrictors, anti-hypertensives, migraine treatments, hypnotics, hyper- or hypoglycemic agents, mineral or nutritional agents, anti-obesity drugs, anabolics and anti-asthmatics, and mixtures thereof.

Preferred therapeutic agents are anti-cancer drugs, preferably antineoplastic agents. The antineoplastic agents may be selected from the group consisting of alkaloids, alkylating agents such as alkyl sulfonates, aziridines, ethylenimines and methylmelamines, nitrogen mustards, nitrosoureas, antibiotics and analogs, preferably anthracyclins, antimetabolites such as folic acid analogs, folic acid antagonists, purine analogs and pyrimidine analogs, enzymes, immunomodulators, immunotoxins, monoclonal antibodies, and platinum complexes.

The particularly preferred antineoplastic agent can be selected from the group consisting of 9-amino camptothecin, docetaxel, ecteinascidins, etoposide, irinotecan, paclitaxel, rubitecan, teniposide, topotecan, vinblastine, vincristine, vindesine, busulfan, improsulfan, piposulfan, carboquone, uredepa, altretamine, triethylenemelamine, triethylenephosphoramide, triethylenethiophosphoramide, chlorambucil, chlomaphazine, cyclophosphamide, estramustine, ifosfamide, mechlorethamine, mechlorethamine oxide hydrochloride, melphalan, novembichin, perfosfamide, phenesterine, prednimustine, trichlormethine, trofosfamide, uracil mustard, carmustine, chlorozotocin, fotemustine, lomustine, nimustine, ranimustine, dacarbazine, mannomustine, mitobronitol, mitolactol, pipobroman, temozolomide, aclacinomycins, anthramycin, azaserine, bleomycins, cactinomycin, carubicin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycins, peplomycin, pirarubicin, plicamycin, porfiromycin, puromycin, streptonigrin, streptozocin, TNP-470, tubercidin, valrubicin, zinostatin, zorubicin, denopterin, edatrexate, methotrexate, nolatrexed, pemetrexed, piritrexim, pteropterin, ralitrexed, trimetrexate, cladribine, fludarabine, 6-mercaptopurine, thiamiprine, thioguanine, tiazofurin, ancitabine, azacitidine, 6-azauridine, capecitabine, carmofur, cytarabine, decitabine, doxifluridine, emitefur, enocitabine, floxuridine, fluorouracil, gemcitabine, tegafur, L-asparaginase, ranpirnase, bropirimine, interferon-α, interferon-γ, interleukin-2, lentinan, propagermanium, PSK®, roquinimex, sizofuran, ubenimex, denileukin diftitox, alemtuzumab, edrecolomab, gemtuzumab ozogamicin, ibritumomab tiuxetan, rituximab, tositumomab $^{131}$I, trastuzumab, carboplatin, cisplatin, lobaplatin, miboplatin, oxaliplatin, amsacrine, arsenic trioxide, bisantrene, defosfamine, demecolcine, diaziquone, eflornithine, elliptinium acetate, etoglucid, fenretinide, flavopiridol, gallium nitrate, hydroxyurea, imatinib, liarozole, lonidamine, miltefosine, mitoguazone, mitoxantrone, mopidamol, nitracrine, pentostatin, phenamet, podophyllinic acid 2-ethylhydrazide, procarbazine, razoxane, sobuzoxane, spirogermanium, tenuazonic acid, tirapazamine, triaziquone, and urethane.

The drug targeting system of the invention can be produced by a high pressure homogenization-solvent evaporation technique or by a double emulsion technique.

A preferred method for preparing a drug-loaded PLA- and/or PLGA nanoparticle drug targeting system containing TPGS comprises the steps of:

solubilizing poly(DL-lactide) and/or poly(DL-lactide-co-glycolide), at least one pharmacologically active substance, and optionally a lipid compound in an organic solvent to obtain an organic phase;
  pouring the organic phase into an aqueous solution containing TPGS;
  emulsifying the mixture to obtain a primary emulsion;
  homogenizing the primary emulsion;
  removing the organic solvent from the primary emulsion; and
  filtering the resulting nanosuspension comprising drug-loaded nanoparticles.

Another preferred method for preparing a drug-loaded PLA- and/or PLGA-nanoparticle drug targeting system containing TPGS comprises the steps of:

solubilizing poly(DL-lactide) and/or poly(DL-lactide-co-glycolide) in an organic solvent to obtain an organic phase;
  dissolving at least one pharmacologically active substance in an aqueous solution;
  pouring the aqueous solution into the organic phase;
  emulsifying the mixture to obtain a primary emulsion;
  pouring the primary emulsion into an aqueous solution of TPGS;

homogenizing the mixture of primary emulsion and aqueous solution of TPGS;
removing the organic solvent from the mixture of primary emulsion and aqueous solution of a stabilizing agent;
filtering the resulting nanosuspension comprising drug-loaded nanoparticles.

A preferred method for preparing a drug-loaded PLA- and/or PLGA-nanoparticle drug targeting system being coated with poloxamer 188 comprises the steps of:
solubilizing poly(DL-lactide) and/or poly(DL-lactide-co-glycolide), at least one pharmacologically active substance, and optionally a lipid compound in an organic solvent to obtain an organic phase;
pouring the organic phase into an aqueous solution optionally comprising a stabilizing agent;
emulsifying the mixture to obtain a primary emulsion;
homogenizing the primary emulsion;
removing the organic solvent from the primary emulsion;
filtering the resulting nanosuspension comprising drug-loaded nanoparticles; and
coating the nanoparticles with poloxamer 188.

Another preferred method for preparing a drug-loaded PLA- and/or PLGA-nanoparticle drug targeting system being coated with poloxamer 188 comprises the steps of:
solubilizing poly(DL-lactide) and/or poly(DL-lactide-co-glycolide) in an organic solvent to obtain an organic phase;
dissolving at least one pharmacologically active substance in an aqueous solution;
pouring the aqueous solution into the organic phase;
emulsifying the mixture to obtain a primary emulsion;
pouring the primary emulsion into an aqueous solution of a stabilizing agent;
homogenizing the mixture of primary emulsion and aqueous solution of a stabilizing agent;
removing the organic solvent from the mixture of primary emulsion and aqueous solution of a stabilizing agent;
filtering the resulting nanosuspension comprising drug-loaded nanoparticles; and
coating the nanoparticles with poloxamer 188.

Preferred diagnostic agents and therapeutic agents, in particular antineoplastic agents for the production of the drug targeting system of the invention were specified herein before.

The preferred organic solvents for the production of the drug targeting system of the invention are selected from the group consisting of dichloromethane and chloroform. It is also possible to use ethyl acetate as a solvent for the production of PLA- and/or PLGA-nanoparticles, provided that the optional stabilizing agent is soluble in ethyl acetate.

It is further possible to use mixtures of dichloromethane and ethyl acetate.

The preferred lipid compound is selected from the group consisting of cetyl phosphate, potassium cholesteryl sulphate and tocoperyl succinate.

The preferred stabilizing agents are emulsifiers, surfactants or counterions. The preferred stabilizing agents are selected from the group consisting of polyvinyl alcohols, serum albumins, γ-cyclodextrin, and tocopheryl polyethylene glycol 1000 succinate (TPGS), wherein the polyvinyl alcohols preferably have a molecular weight of 30-70 kDa, and the particularly preferred serum albumin is human serum albumin.

For storage, the resulting nanosuspension of drug-loaded nanoparticles can be freeze dried before they are coated with poloxamer 188. Preferably a cryoprotecting agent is added to the nanosuspension before it is freeze-dried. A suitable cryoprotecting agent is mannitol, which is preferably added to the nanosuspension in an amount of 5% (w/v).

Coating of the drug-loaded nanoparticles is preferably carried out with a solution of poloxamer 188 in a solution and by allowing sufficient time to allow the surfactant to coat the drug-loaded nanoparticles.

The drug targeting system for administering a pharmacologically active substance to the central nervous system of a mammal across its blood brain barrier, wherein the drug targeting system comprises nanoparticles made of poly(DL-lactide) and/or poly(DL-lactide-co-glycolide), a therapeutic agent, and TPGS or a poloxamer 188 surfactant coating deposited on the drug-loaded nanoparticles can be used to treat diseases or disorders of the central nervous system of a mammal. The drug targeting system is particularly suitable for administering pharmacologically active substances which have central nervous system activity but cannot cross the blood-brain barrier of a mammal without being modified or being associated with a carrier.

The drug targeting system of the invention is particularly useful for the treatment of neuronal cancers, because it can deliver antineoplastic agents across the blood-brain barrier to target these anti-cancer drugs to the CNS.

The drug targeting system of the invention is to be administered such that it can enter the blood stream whereby the drug reaches and crosses the blood-brain barrier. Preferably, the drug targeting system of the invention is administered orally or by injection, most preferably by intravenous injection.

EXAMPLES

1. Preparation of Nanoparticulate Formulations

Various grades of LACTEL® polymers—poly(DL-lactide) (PLA) and poly(DL-lactide-co-glycolide) (PLGA)—were purchased from Absorbable Polymers, USA; doxorubicin hydrochloride was a generous gift from Sicor, Rho, Italy; cetyl phosphate, potassium cholesteryl sulfate, polyvinyl alcohol (PVA) (MW 30-70 kDa), and human serum albumin (HSA) were purchased from Sigma; D-α-tocopheryl polyethylene glycol 1000 succinate (TPGS) was purchased from Eastman Chemical Company, USA.

The drug-loaded PLA and PLGA nanoparticles were produced either utilizing the high pressure homogenization-solvent evaporation technique or the double emulsion technique.

For high pressure homogenization-solvent evaporation, the polymer and the drug were usually dissolved in dichloromethane. This organic phase was slowly poured under stirring into an aqueous solution of a stabilizer (PVA or HSA). The mixture was emulsified using a high speed shear homogenizer (ULTRA-TURRAX® T-25 (IKA)). The obtained primary emulsion was then passed through the high-pressure homogenizer (APV Micron Lab 40; Gaulin GmbH, Germany) at 400 bar. The organic solvent was removed by slow evaporation at ambient temperature and normal pressure under stirring (3 hours), or by quick evaporation at reduced pressure (rotary evaporator BUCHI R-200). During the process, the nanodroplets were solidified in the aqueous system. The obtained nanosuspension was filtered through a glass-sintered filter, and 5% w/v mannitol was added as a cryoprotecting agent. Then the nanosuspension was filled in vials, frozen at −35° C.), and freeze-dried.

Lipid compounds such as cetyl phosphate, potassium cholesteryl sulfate, or tocopheryl succinate were used as emulsifiers and/or counter-ions in some preparations. In this case, the polymer and the lipid component were solubilized in the organic solvent (dichloromethane or chloroform) and the drug was dissolved in water. The organic and aqueous solutions were mixed and incubated for 12 hours at ambient temperature. The mixture was then poured into a stirred aqueous solution (25 ml) containing a stabilizer and then further processed as described above.

For the double emulsion technique, the polymer (500 mg) was usually dissolved in dichloromethane (5 ml) (1 hour under magnetic stirring). The drug (50 mg) was dissolved in water (2 ml). The aqueous solution was added dropwise to the organic phase. The mixture was emulsified using an ULTRA-TURRAX® T-25 (2 minutes at 19,500 rpm). The obtained w/o emulsion was added to 25 ml of a 1% aqueous solution of a stabilizing agent (PVA, HSA, or TGPS) and then emulsified using an ULTRA-TURRAX® T-25. The resulting coarse emulsion was then passed through a high-pressure homogenizer (APV Micron Lab 40) at a pressure of 600 bar. The homogenization step was repeated several times to produce stable w/o/w emulsions. The organic solvent was removed from the w/o/w emulsion by slow evaporation at ambient temperature and normal pressure (magnetic stirrer, 3 hours). The obtained nanosuspension was filtered through a glass-sintered filter and 5% w/v of mannitol was added as cryoprotecting agent. Then the emulsion was filled in vials (1 ml/vial), frozen (−35° C.), and freeze-dried.

Dichloromethane is a typical solvent used in preparation of PLA/PLGA nanoparticles. However, it is also possible to use ethyl acetate or mixtures of dichloromethane and ethyl acetate. However, certain counterions are not soluble in ethyl acetate. In these cases ethyl acetate is an inappropriate solvent for the manufacturing of PLA/PLGA nanoparticles.

The obtained formulations were tested for resuspendability, particle size, drug loading (theoretical), and drug content.

The obtained nanoparticulate formulation was considered suitable if a uniform and stable colloidal system was observed after reconstitution of the freeze-dried nanoparticles with water. Resuspendability of the nanoparticles was assessed visually. Therefore, the content of a vial containing a freeze-dried formulation was reconstituted to the initial volume (2 ml) with water, and the vial was shaken gently for 2-4 minutes. Suitable reconstituted formulations become opalescent liquids without visible agglomerates or precipitations. Samples containing visible agglomerates or precipitate were discarded.

The size of the nanoparticles was measured by photon correlation spectroscopy (PCS) in that an aliquot of the reconstituted formulation (50 µl) was transferred into a Nanosizer test tube containing 3 ml of double distilled water. The tube was shaken and then inserted into a Coulter N4MD Nanosizer (Coulter Electronics, U.K). The working parameters were:

| | |
|---|---|
| Scattering angle: | 90° |
| Temperature: | 25° |
| Viscosity: | 0.01 poise |
| Refractive index | 1.333 |

Drug loading was measured in the reaction mixture after the filtration step or in the freeze-dried formulation after reconstitution. The method for determining the drug load comprises separation of the nanoparticles by ultrafiltration and a subsequent quantitative analysis of a free drug in the filtrate by spectrophotometry.

For determining the drug load of a nanoparticulate formulation, the content of a vial with a freeze-dried formulation was reconstituted in 1 ml of water; 400 µl were transferred to a microcentrifuge filter (MICROCON® 30 kDa, Millipore), and the nanoparticles were separated by centrifugation at 16,000 rpm for 50 min. 100 µl of the clear filtrate were transferred to a cuvette containing 3 ml of double distilled water, and the absorption was measured by utilizing a spectrophotometer (Spectronics Heλios, Thermospectronic, GB) against water at 480 nm. The concentration of a drug in the sample was determined using an appropriate calibration graph.

Relative drug loading (% of total drug amount) was calculated as follows:

$$\% \text{ Drug loading} = \frac{Ci - Cf}{Ci} \times 100\%, \text{ where}$$

$C_i$=initial drug concentration in the polymerization medium (mg/ml);

$C_f$=drug concentration in the filtrate (mg/ml).

The method for determination of drug content (mg/vial) is a quantitative analysis after the complete dissolution of the freeze-dried formulation. The concentration of the drug in solution is measured by spectrophotometry using a calibration curve.

To determine the drug content, the content of a vial with a freeze-dried formulation was dissolved in 2 ml of dimethylsulfoxide (3 h, ambient temperature); 100 µl of this solution were transferred into a spectrophotometer cuvette containing 3 ml of double distilled water, and absorption was measured at 480 nm against water by utilizing a spectrophotometer (Spectronics Heλios; Thermospectronic, GB). The concentration of a drug in the sample was determined using the appropriate calibration graph.

Preparation 1

Nanoparticles were prepared by a high pressure homogenization-solvent evaporation technique. 250 mg of the polymer (PLGA 75:25, MW 90,000-126,000 Da) and 25 mg doxorubicin were dissolved in 5 ml of dichloromethane. The organic phase was poured into a stirred aqueous solution (25 ml) containing 0.5% of PVA as stabilizing agent and the mixture was emulsified using an ULTRA-TURRAX® T-25 (2 min; 15,100 rpm). The resulting primary emulsion was further homogenized using a high pressure homogenizer (APV Micron Lab 40) at 400 bar. Dichloromethane was evaporated under reduced pressure (rotor evaporator BUCHI® R-200). The resulting nanosuspension was filtered through a glass-sintered filter and freeze-dried after addition of 5% w/v mannitol as a cryoprotector. The freeze-dried formulation was completely resuspendable. The particle size measured by PCS was 140-220 nm, doxorubicin loading was 40%.

Preparation 2

Nanoparticles were prepared by a double emulsion technique. 500 mg of the polymer (PLGA with acid end groups, inherent viscosity: η=0.20 dL/g) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 minutes; 19,500 rpm). The resulting primary emulsion was poured into 25 ml of a 1% PVA aqueous solution, and the mixture was again homogenized utilizing the ULTRA-TURRAX® T-25, and then passed three times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 110-160 nm, doxorubicin loading was 75%.

Preparation 3

Nanoparticles were prepared by a double emulsion technique. 500 mg of the polymer (PLGA 75:25, MW 90,000-126,000 Da) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 min; 19,500 rpm). The resulting primary emulsion was poured into 25 ml of a 1% PVA aqueous solution, this mixture was again homogenized utilizing the ULTRA-TURRAX® T-25, and then passed four times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v of mannitol as cryoprotecting agent. The freeze-dried formulation was completely resuspendable. The particle size measured by PCS was 160-330 nm, doxorubicin loading was 47%.

Preparation 4

Nanoparticles were prepared by a double emulsion technique. 500 mg of the polymer (PLA, $\eta=0.36$ dL/g) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 minutes; 19,500 rpm). The resulting primary emulsion was poured into 25 ml of a 1% PVA aqueous solution and the mixture was again homogenized utilizing the ULTRA-TURRAX® T-25, and then passed four times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 126-210 nm, doxorubicin loading was 42%.

Preparation 5

Nanoparticles were prepared by a double emulsion technique. 500 mg of the polymer (PLGA with acid end groups, $\eta=0.20$ dL/g) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 min; 19,500 rpm). The resulting primary emulsion was poured into 25 ml of a 1% PVA aqueous solution, the mixture was again homogenized utilizing the ULTRA-TURRAX® T-25, and then passed three times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 140-200 nm, doxorubicin loading was 73%.

Preparation 6

Nanoparticles were prepared by a double emulsion technique. 500 mg of the polymer (PLGA 50:50 with acid end groups, $\eta=0.20$ dL/g) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 min; 19,500 rpm). The resulting primary emulsion was poured into 25 ml of a 1% PVA aqueous solution, the mixture was again homogenized utilizing the ULTRA-TURRAX® T-25, and then passed three times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 130-190 nm, doxorubicin loading was 67%.

Preparation 7

Nanoparticles were prepared by a double emulsion technique. 500 mg of the polymer (PLGA 50:50 with acid end groups, $\eta=0.20$ dL/g) were solubilized in 3 ml dichloromethane. 50 mg doxorubicin hydrochloride were dissolved in 2 ml 0.001N HCl. The aqueous solution was poured into the organic phase and the mixture was emulsified using an ULTRA-TURRAX® T-25 (2 min; 20,100 rpm). The resulting primary emulsion was poured into 25 ml of a 1% PVA aqueous solution, the mixture was again homogenized utilizing the ULTRA-TURRAX® T-25, and then passed four times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 125-185 nm, doxorubicin loading was 69%.

Preparation 8

Nanoparticles were prepared by a double emulsion technique. 500 mg of the polymer (PLGA 50:50 with acid end groups, $\eta=0.20$ dL/g) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 minutes; 22,600 rpm). The resulting primary emulsion was poured into 25 ml of a 1% HSA aqueous solution, the mixture was again homogenized utilizing the ULTRA-TURRAX® T-25, and then passed four times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 100-200 nm, doxorubicin loading was 40%.

Preparation 9

Nanoparticles were prepared by high pressure homogenization-solvent evaporation technique. 250 mg of the polymer (PLA, MW 90,000-126,000 Da) and 15.1 mg cetyl phosphate were solubilized in 4 ml dichloromethane. 21.8 mg doxorubicin hydrochloride were dissolved in 2 ml water. The organic and aqueous solutions were mixed and incubated for 12 hours at ambient temperature. Then the mixture was poured into a stirred aqueous solution (25 ml) containing 1% of HSA as stabilizing agent and emulsified using an ULTRA-TURRAX® T-25 (2 minutes; 19,100 rpm). The resulting primary emulsion was passed four times through a high pressure homogenizer (APV Micron Lab 40) at 600 bar. Dichloromethane was evaporated under reduced pressure (rotor evaporator BUCHI® R-200). The resulting nanosuspension was filtered through a glass-sintered filter and freeze-dried after addition of 5% w/v mannitol as cryoprotecting agent. The freeze-dried formulation was completely resuspendable. The particle size measured by PCS was 160-240 nm, doxorubicin loading was 60%.

Preparation 10

Nanoparticles were prepared by a double emulsion technique. 500 mg of the polymer (PLGA 50:50 with acid end groups, η=0.20 dL/g) were solubilized in 3 ml dichloromethane. 25 mg doxorubicin hydrochloride were dissolved in 2 ml 0.001N HCl. The aqueous solution was poured into the organic phase, and the mixture was emulsified using an ULTRA-TURRAX® T-25 (2 min; 19,900 rpm). The resulting primary emulsion was poured into 25 ml of a 1% TGPS aqueous solution, the mixture was again homogenized utilizing the ULTRA-TURRAX® T-25, and then passed four times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 300-380 nm, doxorubicin loading was 45%.

Preparation 11

Nanoparticles were prepared by high pressure homogenization-solvent evaporation technique. 250 mg of the polymer (PLA, 0.34 dL/g) and 21.2 mg potassium cholesteryl sulfate were solubilized in 5 ml chloroform. 21.8 mg doxorubicin hydrochloride were dissolved in 2 ml water. The organic and aqueous solutions were mixed and incubated for 12 hours at ambient temperature. The mixture was then poured into a stirred aqueous solution (23 ml) containing 1% of PVA as stabilizing agent and emulsified using an ULTRA-TURRAX® T-25 (2 minutes; 19,100 rpm). The resulting primary emulsion was passed four times through a high pressure homogenizer (APV Micron Lab 40) at 600 bar. Dichloromethane was evaporated under reduced pressure (rotor evaporator BUCHI® R-200). The resulting nanosuspension was filtered through a glass-sintered filter and freeze-dried after addition of 5% w/v mannitol as cryoprotecting agent. The freeze-dried formulation was completely resuspendable. The particle size measured by PCS was 500-600 nm, doxorubicin loading was 89%.

Preparation 12

Nanoparticles were prepared by high pressure homogenization-solvent evaporation technique. 250 mg of the polymer (PLA, 0.34 dL/g) and 22.9 mg D-α-tocopheryl succinate were solubilized in 5 ml chloroform. 25.4 mg doxorubicin hydrochloride were dissolved in 2 ml water. The organic and aqueous solutions were mixed and incubated for 12 hours at ambient temperature. Then the mixture was poured into a stirred aqueous solution (23 ml) containing 0.5% of PVA as stabilizing agent, and emulsified using an ULTRA-TURRAX® T-25 (2 minutes; 23,600 rpm). The resulting primary emulsion was passed four times through a high pressure homogenizer (APV Micron Lab 40) at 600 bar. Chloroform was evaporated under reduced pressure (rotor evaporator BUCHI® R-200). The resulting nanosuspension was filtered through a glass-sintered filter and freeze-dried after addition of 5% w/v mannitol as cryoprotecting agent. The freeze-dried formulation was completely resuspendable. The particle size measured by PCS was 224-368 nm, doxorubicin loading was 50%.

Preparation 13

Nanoparticles were prepared by high pressure homogenization-solvent evaporation technique. 250 mg of the polymer (PLA, 0.34 dL/g) and 14.9 mg cetyl phosphate were solubilized in 5 ml chloroform. 24.5 mg doxorubicin hydrochloride were dissolved in 2 ml water. The organic and aqueous phases were mixed and incubated for 12 hours at ambient temperature. Then the mixture was poured into a stirred aqueous solution (23 ml) containing 0.5% of PVA as stabilizing agent, and emulsified using an ULTRA-TURRAX® T-25 (2 min; 23,600 rpm). The resulting primary emulsion was passed four times through a high pressure homogenizer (APV Micron Lab 40) at 600 bar. Chloroform was evaporated under reduced pressure (rotor evaporator BUCHI R-200). The resulting nanosuspension was filtered through a glass-sintered filter and freeze-dried after addition of 5% w/v mannitol as cryoprotecting agent. The freeze-dried formulation was completely resuspendable. The particle size measured by PCS was 200-250 nm, doxorubicin loading was 53%.

Preparation 14

Nanoparticles were prepared by a double emulsion technique. 500 mg of the polymer (PLGA 50:50 with acid end groups, η=0.67 dL/g) were solubilized in 3 ml dichloromethane. 20 mg doxorubicin hydrochloride and 45 mg γ-cyclodextrin were dissolved in 3 ml of water. An aqueous solution was poured into an organic phase, and the mixture was emulsified using an ULTRA-TURRAX® T-25 (2 minutes; 23,600 rpm). The resulting primary emulsion was poured into 25 ml of a 0.5% PVA aqueous solution, the mixture was again homogenized utilizing the ULTRA-TURRAX® T-25, and then passed four times through a high pressure homogenizer (APV Micron Lab 40) at 600 bar. Dichloromethane was evaporated by stirring the emulsion at ambient temperature for 3 hours. The resulting nanosuspension was filtered through a glass-sintered filter and freeze-dried after addition of 5% w/v mannitol as cryoprotecting agent. The freeze-dried formulation was completely resuspendable. The particle size measured by PCS was 200-250 nm, doxorubicin loading was 44%.

2. Animal Studies

Orthotopic Tumour Model System. An experimental system was based on intracranially implanted 101/8 glioblastoma in rats. This tumour was initially produced by local injection of an α-dimethylbenzanthracene (DMBA) pellet into a Wistar rat cerebellum and maintained by continuous passages by intracerebral implantation. For long-term storage the tumour tissue was kept at −196° C. and was propagated by injection into the brains of rats.

The 101/8 glioblastoma was previously employed for experimental chemotherapy using doxorubicin loaded in the surface-modified poly(butyl cyanoacrylate nanoparticles). The tumour has a stable monomorphous structure and shows the characteristic histological picture of aggressive glioblastoma with fast diffuse growth in the brain parenchyma and a rather low tendency towards necrosis. The transplantability of the tumour was about 100%, yielding a predictable symptom-free life span after inoculation. The transplantation of 101/8 glioblastoma in the present study was performed using fresh tumour tissue. This technique was chosen to preserve the major typical features of the parent tumour, especially its antigenic structure and differentiation.

Adult male Wistar rats weighing 200-250 g were acclimatized for 1 week and caged in groups of five. They were fed ad libitum with standard laboratory food and water. For tumour implantation, animals were deeply anaesthetised by intraperitoneal injections of pentobarbital (50 mg/kg). Through a midline sagittal incision, a burr hole of 1.5 mm in diameter was made with a dental drill at a point 2 mm posterior to the right coronal suture and 2 mm lateral to the sagittal midline. Tumour material (approximately $10^6$ cells) from the frozen stock was introduced into a tuberculin syringe linked to a 21-gauge needle. The tip was placed 4 mm below the bone surface and the tumour tissue was injected into the bottom of the right lateral ventricle. The scalp incision was sewn or closed with glue. After development of pronounced clinical signs of the disease (usually day 14) the animals were sacrificed by carbon dioxide asphyxiation, then decapitated. The brain was immediately removed. The tumour was excised and chopped with a scalpel; a tumour implant (5 mg) was inoculated into the brain of new experimental animals, as described above. The appropriate coordinates were confirmed and the technique refined by repeated pilot experiments.

The nanoparticles to be used for animal testing were based on low molecular PLGA 50:50 with acid end groups (η=0.20 dl/g), and loaded with doxorubicin utilizing doxorubicin hydrochloride. A drug-to-polymer ratio of 1:10 was used for the preparation of the doxorubicin-loaded PLGA nanoparticles. The particle size was measured to be 144±12 nm, doxorubicin loading was 75.5%.

In order to obtain surfactant-coated particles, the freeze-dried formulation was resuspended in a 1% aqueous solution of either surfactant (PLURONIC® F68, PLURONIC® P85 and polysorbate 80). The resulting preparations were then incubated for 30 minutes under stirring and used within 2 hours.

Tumour-bearing rats were randomly divided into six groups (n=10) and received one of the following formulations: 1) untreated control; 2) doxorubicin in saline (DOX); 3) doxorubicin in 1% PLURONIC® F68 (Dox/F68); 4) doxorubicin loaded PLGA nanoparticles (DOX-PLGA); 5) doxorubicin loaded PLGA nanoparticles coated with PLURONIC® F68 (DOX-PLGA/F68); 6) doxorubicin loaded PLGA nanoparticles coated with polysorbate 80 (not shown); 7) doxorubicin loaded PLGA nanoparticles coated with PLURONIC® P85 (results not shown in FIG. 1).

These preparations were injected intravenously into the tail vein using the following dose regimen: 3×1.5 mg/kg on day 2, day 5, and on day 8 after tumour implantation.

The animals were followed up for 100 days post treatment; then surviving animals were sacrificed and necropsied. Results are shown in FIG. 1.

In the control group, all animals died within 19 days after tumor implantation. Doxorubicin loaded PLGA nanoparticles coated with poloxamer 188 considerably enhanced survival of tumor-bearing rats: 40% of the animals (4/10) survived for 100 days. Only one animal on the group treated with doxorubicin in a 1% solution of poloxamer 188 survived. Absence of tumor in these animals was confirmed by morphological examination.

In contrast to the results obtained with doxorubicin-loaded PLGA nanoparticles coated with poloxamer 188, coating of doxorubicin-loaded nanoparticles with either polysorbate 80 or PLURONIC® P85 failed to enhance the efficacy of the nanoparticle-bound doxorubicin (data not shown).

In a second set of experiments, formulations comprising doxorubicin-loaded PLGA nanoparticles based on PLGA with acid end groups (PLGA-COOH), and containing TPGS as stabilizer (Dox/PLGA-COOH/TPGS; preparation 10) or being coated with TPGS (Dox/PLGA-COOH+TPGS) were investigated for their in-vivo effect on 101/8 glioblastoma-bearing rats. The latter formulation was obtained by resuspending nanoparticles according to preparation 5 in 0.5% TPGS before the nanoparticles were injected into the animals.

Figure 2:
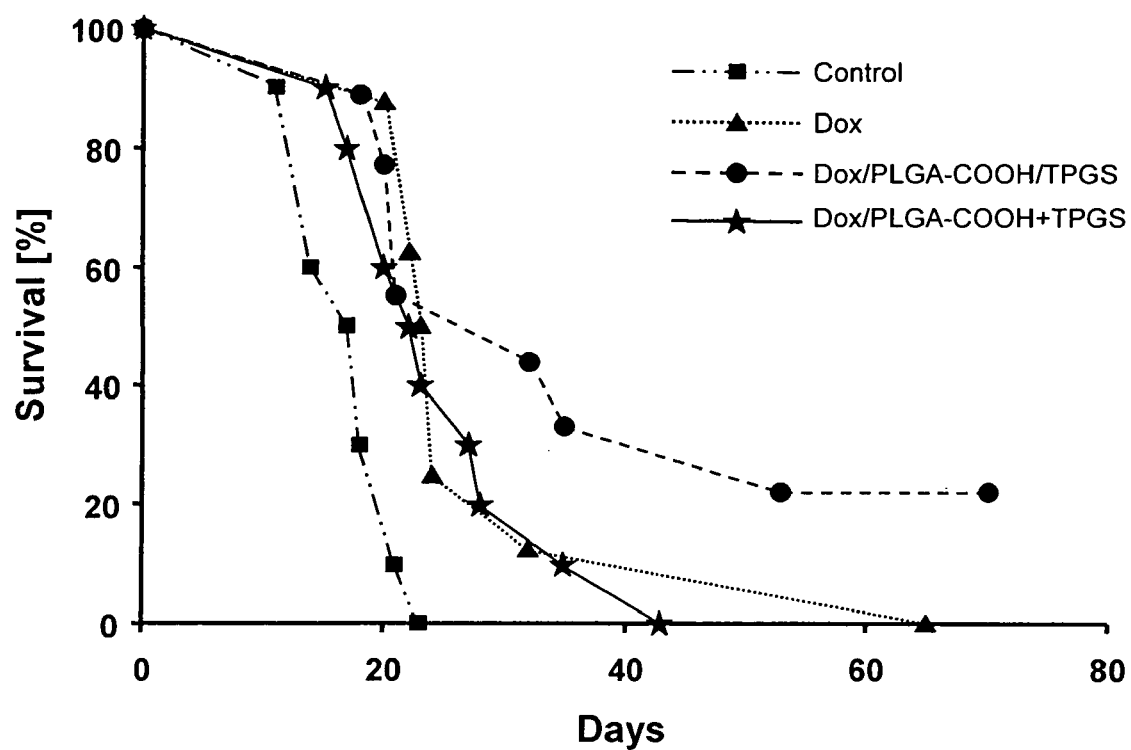
FIG. 2 shows a graph which illustrates the survival of rats bearing intracranial 101/8 glioblastoma after chemotherapy with various nanoparticle preparations comprising doxorubicin and TPGS.

The result of this set of experiments is shown in FIG. 2. It can be seen that the nanoparticles according to preparation 10, i.e. containing TPGS as stabilizer, considerably increased survival time of tumor-bearing rats and permitted long-term survival of 20% of the tumor-bearing rats used for this experiment. Nanoparticles according to preparation 5 that were coated with TPGS prior to their use were not effective.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A method of preparing a drug targeting system for administering a pharmacologically active substance to the central nervous system of a mammal across the blood brain barrier of the mammal, the method comprising the steps of:
    solubilizing poly(DL-lactide) and/or poly(DL-lactide-co-glycolide), at least one pharmacologically active substance, and a lipid compound selected from the group of lipid compounds consisting of cetyl phosphate, potassium cholesteryl sulphate and tocopheryl succinate, in an organic solvent to obtain an organic phase;
    pouring the organic phase into an aqueous solution containing TPGS to form a mixture;
    emulsifying the mixture to obtain a primary emulsion;
    homogenizing the primary emulsion;
    removing the organic solvent from the primary emulsion to form a nanosuspension comprising drug-loaded nanoparticles; and
    filtering the resulting nanosuspension comprising drug-loaded nanoparticles.

2. The method of preparing a drug targeting system for administering a pharmacologically active substance to the central nervous system of a mammal across the blood brain barrier of the mammal according to claim 1, said method further comprising the step of coating the nanoparticles with poloxamer 188.

3. The method according to claim 1, wherein the pharmacologically active substance is selected from the group consisting of a therapeutic agent and a diagnostic agent.

4. The method according to claim 3, wherein the therapeutic agent is selected from the group consisting of drugs acting at synaptic and neuroeffector junctional sites; general and local analgesics and anesthetics; hypnotics and sedatives; drugs for the treatment of psychiatric disorders; drugs for the treatment of depression; drugs for the treatment of schizophrenia; anti-epileptics and anticonvulsants; drugs for treating Huntington's disease, aging and Alzheimer's disease; excitatory amino acid antagonists and neurotropic factors and neuroregenerative agents; trophic factors; drugs aimed at the treatment of CNS trauma or stroke; drugs for the treatment of addiction and drug abuse; autacoids and anti-inflammatory drugs; chemotherapeutic agents for parasitic infections and microbial diseases; immunosuppressive agents and anti-cancer drugs; hormones and hormone antagonists; heavy metals and heavy metal antagonists; antagonists for nonmetallic toxic agents; cytostatic agents for the treatment of cancer; diagnostic substances for use in nuclear medicine; immunoactive and immunoreactive agents; transmitters and their respective receptor agonists and receptor antagonists, their respective precursors or metabolites; antibiotics, antispasmodics, antihistamines, antinauseants, relaxants, stimulants, "sense" and "anti-sense" oligonucleotides, cerebral dilators, psychotropics, anti-manics, vascular dilators and constrictors, anti-hypertensives, agents for migraine treatment, hypnotics, hyper- or hypo-glycemic agents, mineral or nutritional agents, anti-obesity drugs, anabolics and anti-asthmatics, and mixtures thereof.

5. The method according to claim 3, wherein the diagnostic agent is useful in the diagnosis for nuclear medicine and/or radiation therapy.

6. The method according to claim 1, further comprising the steps of:
   adding a cryoprotecting agent to said nansuspension; and
   freeze-drying the nanosuspension after the step of adding the cryoprotecting agent.

7. The method according to claim 6, wherein the cryoprotecting agent is mannitol and wherein said cryoprotecting agent is added to the nanosuspension in an amount of 5% (w/v).

* * * * *